US00PP28305P3

(12) United States Plant Patent
Stemkens

(10) Patent No.: US PP28,305 P3
(45) Date of Patent: Aug. 15, 2017

(54) ***STOKESIA* PLANT NAMED 'SYNSTOKHAR'**

(50) Latin Name: *Stokesia laevis*
Varietal Denomination: Synstokhar

(71) Applicant: Henricus Godefridus Wilhelmus Stemkens, Enkhuizen (NL)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 48 days.

(21) Appl. No.: 14/757,310

(22) Filed: Dec. 15, 2015

(65) Prior Publication Data

US 2017/0172045 P1 Jun. 15, 2017

(51) Int. Cl.
*A01H 5/02* (2006.01)

(52) U.S. Cl.
USPC ..... Plt./484

(58) Field of Classification Search
USPC ..... Plt./484
See application file for complete search history.

*Primary Examiner* — June Hwu
(74) *Attorney, Agent, or Firm* — C. A. Whealy

(57) ABSTRACT

A new and distinct cultivar of *Stokesia* plant named 'Synstokhar', characterized by its upright to low spreading plant habit; moderately vigorous to vigorous growth habit; freely branching growth habit; relatively short flowering stems; freely flowering habit; large inflorescences with pale violet-colored ray florets; and good garden performance.

2 Drawing Sheets

Botanical designation: *Stokesia laevis.*
Cultivar denomination: 'SYNSTOKHAR'.

BACKGROUND OF THE INVENTION

The present invention relates to a new and distinct cultivar of *Stokesia* plant, botanically known as *Stokesia laevis* and hereinafter referred to by the name 'Synstokhar'.

The new *Stokesia* plant is a product of a planned breeding program conducted by the Inventor in Enkhuizen, The Netherlands. The objective of the breeding program is to create new hardy and easy to produce *Stokesia* plants with a freely branching habit, relatively short flowering stems and numerous large inflorescences.

The new *Stokesia* plant originated from an open-pollination in August, 2007 in Enkhuizen, The Netherlands of a proprietary selection of *Stokesia laevis* identified as code number MM0959, not patented, as the female, or seed, parent with an unknown selection of *Stokesia laevis* as the male, or pollen, parent. The new *Stokesia* plant was discovered and selected by the Inventor as a single flowering plant within the progeny of the stated open-pollination in a controlled nursery environment in Enkhuizen, The Netherlands in 2008.

Asexual reproduction of the new *Stokesia* plant by vegetative basal cuttings was first conducted in Enkhuizen, The Netherlands in March, 2009. Asexual reproduction by cuttings has shown that the unique features of this new *Stokesia* plant are stable and reproduced true to type in successive generations.

SUMMARY OF THE INVENTION

Plants of the new *Stokesia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Synstokhar'. These characteristics in combination distinguish 'Synstokhar' as a new and distinct *Stokesia* plant:

1. Upright to low spreading plant habit.
2. Moderately vigorous to vigorous growth habit.
3. Freely branching growth habit.
4. Relatively short flowering stems.
5. Freely flowering habit.
5. Large inflorescences with pale violet-colored ray florets.
6. Good garden performance.

Plants of the new *Stokesia* differ from plants of the female parent selection in the following characteristics:

1. Plants of the new *Stokesia* are shorter and not as broad as plants of the female parent selection.
2. Ray florets of plants of the new *Stokesia* are pale violet in color whereas ray florets of plants of the female parent selection are pale blue in color.

Plants of the new *Stokesia* can be compared to plants of *Stokesia laevis* 'Purple Pixie', disclosed in U.S. Plant Pat. No. 19,833. In side-by-side comparisons conducted in Enkhuizen, The Netherlands, plants of the new *Stokesia* differed from plants of 'Purple Pixie' in the following characteristics:

1. Plants of the new *Stokesia* were shorter and broader than plants of 'Purple Pixie'.
2. Plants of the new *Stokesia* were more freely flowering than plants of 'Purple Pixie'.
3. Plants of the new *Stokesia* had larger inflorescences than plants of 'Purple Pixie'.
4. Ray florets of plants of the new *Stokesia* were lighter violet in color than ray florets of plants of 'Purple Pixie'.

Plants of the new *Stokesia* can also be compared to plants of *Stokesia laevis* 'Mels Blue', disclosed in U.S. Plant Pat. No. 23,090. In side-by-side comparisons conducted in Enkhuizen, The Netherlands, plants of the new *Stokesia* differed from plants of 'Mels Blue' in the following characteristics:

1. Plants of the new *Stokesia* were much shorter than and not as broad as plants of 'Mels Blue'.
2. Plants of the new *Stokesia* had larger inflorescences than plants of 'Mels Blue'.
3. Ray florets of plants of the new *Stokesia* were lighter violet in color than ray florets of plants of 'Mels Blue'.

BRIEF DESCRIPTION OF THE PHOTOGRAPHS

The accompanying photographs illustrate the overall appearance of the new *Stokesia* plant showing the colors as true as it is reasonably possible to obtain in colored reproductions of this type. Colors in the photographs may differ slightly from the color values cited in the detailed botanical description which accurately describe the colors of the new *Stokesia* plant.

The photograph on the first sheet is a side perspective view of typical flowering plants of 'Synstokhar' grown in an outdoor nursery.

The photograph on the second sheet is a close-up view of a typical inflorescence of 'Synstokhar'.

DETAILED BOTANICAL DESCRIPTION

The aforementioned photographs and following observations and measurements describe plants grown during the spring, summer and autumn in 7.5-liter containers and in ground beds in an outdoor nursery in Bressingham, United Kingdom and under cultural practices which approximate those generally used in commercial *Stokesia* production. During the production of the plants, day temperatures ranged from 5° C. to 25° C. and night temperatures ranged from −6° C. to 12° C. Plants were one year old when the photographs and description were taken. In the following description, color references are made to The Royal Horticultural Society Colour Chart, 2000 Edition, except where general terms of ordinary dictionary significance are used.

Botanical classification: *Stokesia laevis* 'Synstokhar'.

Parentage:

*Female, or seed, parent*.—Proprietary selection of *Stokesia laevis* identified as code number MM0959, not patented.

*Male, or pollen, parent*.—Unknown selection of *Stokesia laevis*, not patented.

Propagation:

*Type*.—Vegetative basal cuttings.

*Time to initiate roots, summer*.—About ten days at soil temperatures about 15° C.

*Time to produce a rooted young plant, summer*.—About 20 days at soil temperatures about 15° C.

*Root description*.—Medium to fine in thickness, mostly fibrous; typically close to 158C in color, actual color of the roots is dependent on substrate composition, water quality, fertilizers, substrate temperature and physiological age of roots.

*Rooting habit*.—Freely branching; medium density.

Plant description:

*Plant and growth habit*.—Herbaceous perennial; upright to low spreading plant habit; broad inverted triangle; strong and freely branching habit; moderately vigorous to vigorous growth habit.

*Plant height, soil level to top of foliar plane*.—About 20 cm.

*Plant height, soil level to top of floral plane*.—About 25 cm.

*Plant width or spread*.—About 40 cm.

*Flowering stems (peduncles)*.—Length: About 4 cm. Diameter: About 4 mm. Internode length: About 1 cm. Aspect: Mostly upright Strength: Strong. Texture: Sparsely pubescent. Luster: Dull. Color: Close to 138B to 138C becoming closer to 124D with development.

Leaf description:

*Arrangement*.—Alternate, simple.

*Length*.—About 15 cm to 20 cm.

*Width*.—About 3.5 cm.

*Shape*.—Oblanceolate.

*Apex*.—Acute.

*Base*.—Cuneate.

*Margin*.—Entire.

*Texture, upper surface*.—Slightly pubescent.

*Texture, lower surface*.—Glabrous.

*Luster, upper surface*.—Semi-glossy.

*Luster, lower surface*.—Matte.

*Color*.—Developing leaves, upper surface: Close to 137D. Developing leaves, lower surface: Close to 138A. Fully expanded leaves, upper surface: Close to 138A; venation, close to 138B; in the autumn, occasionally lightly flushed with close to 178B. Fully expanded leaves, lower surface: Close to 138B; venation, 138B; color does not change in the autumn.

*Petioles*.—Present on basal leaves only. Length: About 1 cm. Diameter: About 5 mm. Strength: Strong. Texture, upper and lower surfaces: Smooth, glabrous. Luster, upper and lower surfaces: Matte. Color, upper surface: Close to 138B. Color, lower surface: Close to 138C.

Inflorescence description:

*Type and arrangement*.—Composite inflorescence form with Obcordate-shaped ray florets; inflorescences borne on terminal and axillary branches above and beyond the foliar plane; ray and disc florets arranged acropetally on a capitulum.

*Fragrance*.—None detected.

*Flowering response*.—Under natural conditions, plants flower from July to September in the United Kingdom; plants begin flowering about 135 days after planting.

*Inflorescence longevity*.—Inflorescences maintain good substance for about 35 days on the plant; inflorescences persistent.

*Quantity of inflorescences*.—Freely flowering habit with about twelve inflorescences per lateral branch and about 175 inflorescences developing per plant during the flowering season.

*Inflorescence buds*.—Height: About 3 cm. Diameter: About 3 cm. Shape: Globular. Texture: Rough. Luster: Matte. Color: Close to 138C.

*Inflorescence size*.—Diameter: Relatively large, about 7 cm. Depth (height): About 2 cm. Diameter of disc: About 5 cm.

*Receptacles*.—Height: About 2 cm. Diameter: About 2 mm. Shape: Flattened tubular with three free apices. Color: Close to 91B; towards the base, close to 158D.

*Ray florets*.—Quantity and arrangement: About 60 ray florets per inflorescence arranged in about two to three whorls. Orientation: Initially upright, then almost perpendicular to peduncle. Length: About 4.5 cm to 5 cm. Width: About 2 mm. Shape: Obcordate. Apex: Cleft. Base: Cuneate. Margin: Entire; slightly undulate. Texture, upper and lower surfaces: Smooth, glabrous. Luster, upper surface: Slightly glossy, satiny. Luster, lower surface: Matte. Color: When opening, upper surface: Close to 91B; towards the base, close to 158D. When opening, lower surface: Close to 91C; towards the base, close to 158D. Fully opened, upper surface: Close to 91C; towards the base, close to 158D; venation, close to 91B; color does not change with development. Fully opened, lower surface: Close to 91C; towards the base, close to 158D; venation, close to 91C; color becoming closer to 91D with development.

*Disc florets*.—Quantity and arrangement: About 160 massed at the center of the inflorescence. Orientation: Spirally. Length: About 2.5 cm. Width: About 2 mm. Shape: Tubular with three free apices. Apex: Acute. Margin: Entire. Texture, upper and lower surfaces: Smooth; slightly velvety. Luster, upper surface: Slightly glossy. Luster, lower surface: Matte. Color: When opening, upper surface: Close to 91B; towards the base, close to 158D. When opening, lower surface: Close to 91D; towards the base, close to 158D. Fully opened, upper surface: Close to 91B; towards the base, close to 158D; venation, close to 91C; color becoming closer to 91C with development. Fully opened, lower surface: Close to 91D; towards the base, close to 158D; venation, close to 91C; color does not change with development.

*Phyllaries*.—Quantity and arrangement: About 25 per inflorescence arranged in several whorls. Length: About 1 cm. Width: About 5 mm. Shape: Lanceolate. Apex: Acute. Base: Acuminate. Margin: Entire. Texture, upper and lower surfaces: Smooth, glabrous. Luster, upper surface: Slightly glossy. Luster, lower surface: Matte. Color: When opening, upper surface: Close to 138D. When opening, lower surface: Close to 138C. Fully opened, upper and lower surfaces: Close to 138C.

*Reproductive organs*.—Androecium: Present on disc florets only. Quantity of stamens per floret: Numerous. Filament length: About 3 cm. Filament color: Close to 158B. Anther shape: Lanceolate. Anther size: About 6 mm by 1 mm. Anther color: Close to 158B. Pollen amount: Scarce. Pollen color: Close to 158A. Gynoecium: Present on ray and disc florets. Quantity of pistils per floret: One. Pistil length: About 3 cm. Stigma diameter: About 3 mm. Stigma shape: Cleft. Stigma color: Close to 158B. Style length: About 1 cm. Style color: Close to 158A. Ovary color: Close to 158B.

*Seeds and fruits*.—Seed and fruit production have not been observed on plants of the new *Stokesia*.

Disease & pest resistance: Plants of the new *Stokesia* have been observed to have good resistance to Leaf Spot. Plants of the new *Stokesia* have not been observed to be resistant to pests and other pathogens common to *Stokesia* plants.

Garden performance: Plants of the new *Stokesia* have been observed to be tolerant to rain, wind, to tolerate temperatures ranging from about −15° C. to about 25° C., and to be suitable for USDA Hardiness Zones 5 through 9.

It is claimed:

1. A new and distinct *Stokesia* plant named 'Synstokhar' as illustrated and described.

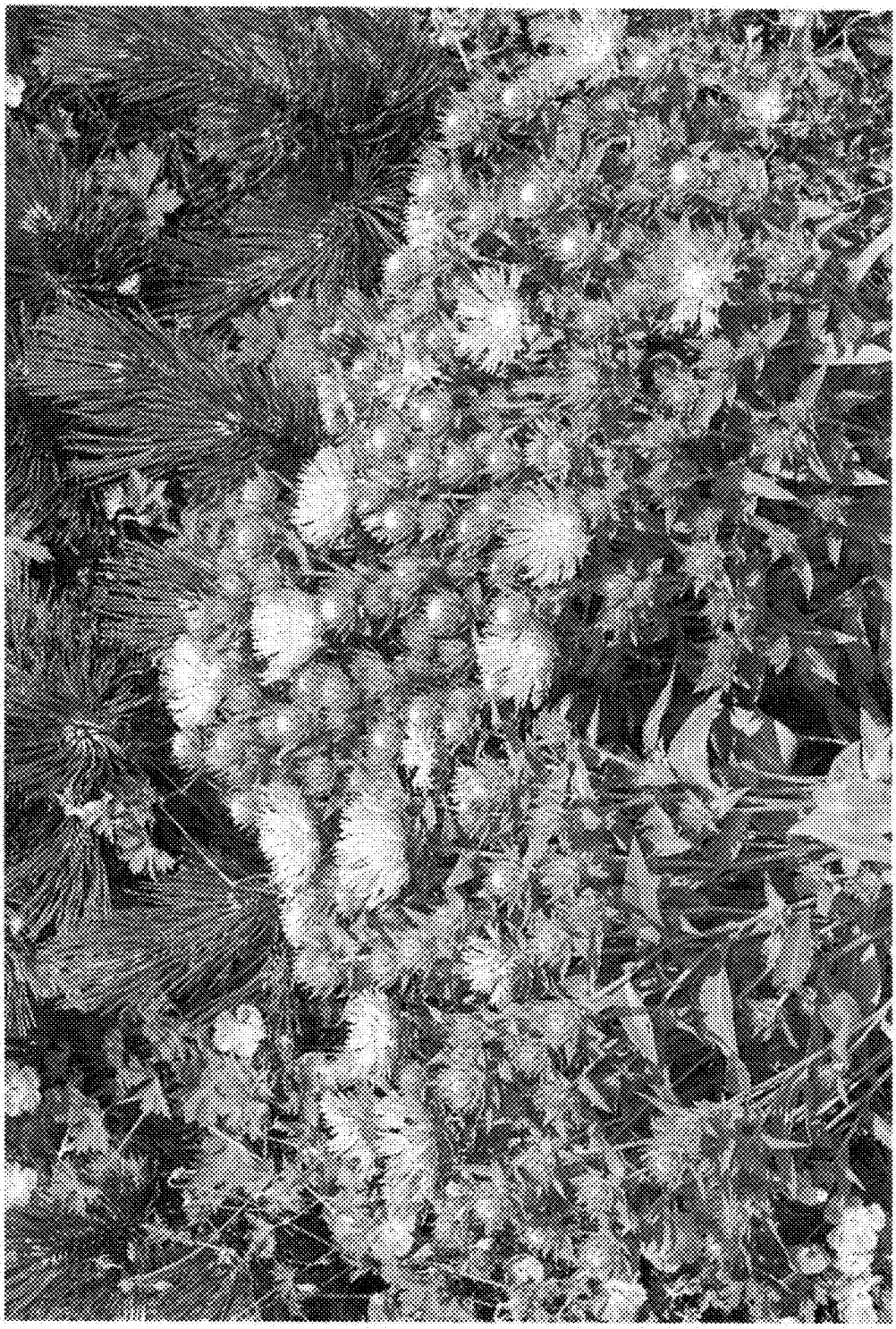

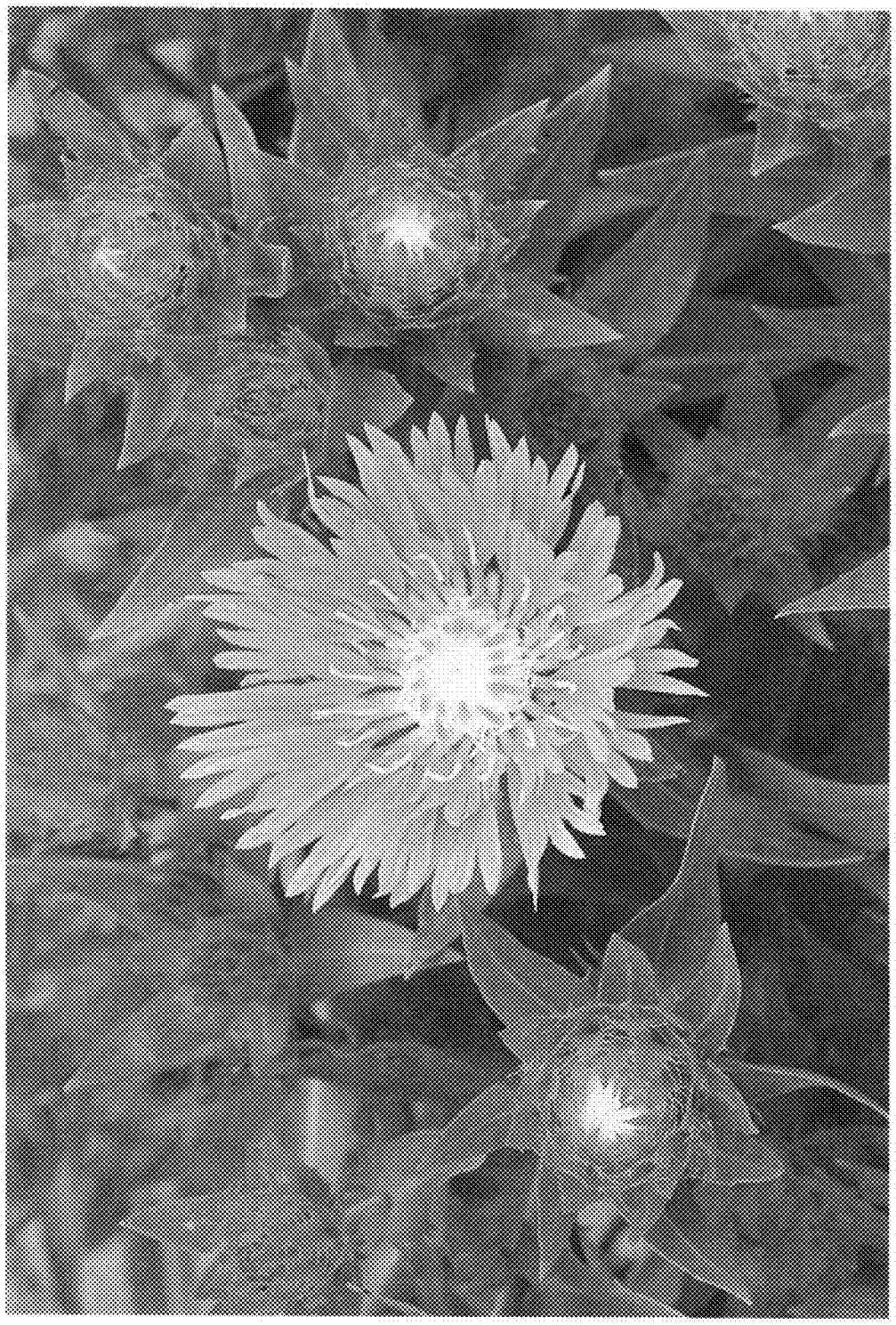

* * * * *